United States Patent
Fadhel (10) Patent No.: US 9,142,781 B2
(45) Date of Patent: Sep. 22, 2015

(54) COMPOUND FOR ORGANIC ELECTRONIC DEVICE

(75) Inventor: Omrane Fadhel, Dresden (DE)

(73) Assignee: NOVALED AG, Dresden (DE)

(*) Notice: Subject to any disclaimer, the term of this patent is extended or adjusted under 35 U.S.C. 154(b) by 9 days.

(21) Appl. No.: 14/124,426

(22) PCT Filed: Jun. 7, 2012

(86) PCT No.: PCT/EP2012/060794
§ 371 (c)(1),
(2), (4) Date: Mar. 11, 2014

(87) PCT Pub. No.: WO2012/168358
PCT Pub. Date: Dec. 13, 2012

(65) Prior Publication Data
US 2014/0174537 A1    Jun. 26, 2014

(30) Foreign Application Priority Data

Jun. 9, 2011 (EP) .................................. 11169313

(51) Int. Cl.
*C07D 471/16* (2006.01)
*H01L 51/00* (2006.01)
*C07D 471/22* (2006.01)
*H01L 51/42* (2006.01)

(52) U.S. Cl.
CPC .......... *H01L 51/0056* (2013.01); *C07D 471/16* (2013.01); *C07D 471/22* (2013.01); *H01L 51/0053* (2013.01); *H01L 51/42* (2013.01); *Y02E 10/549* (2013.01)

(58) Field of Classification Search
CPC .................................................. C07D 471/16
See application file for complete search history.

(56) References Cited

U.S. PATENT DOCUMENTS

| 5,139,909 | A | 8/1992 | Kazmaier et al. |
| 2005/0040390 | A1 | 2/2005 | Pfeiffer et al. |
| 2007/0252140 | A1 | 11/2007 | Limmert et al. |
| 2009/0212280 | A1 | 8/2009 | Werner et al. |

FOREIGN PATENT DOCUMENTS

| EP | 1 795 969 | A1 | | 6/2007 |
| EP | 1795969 | A1 | * | 6/2007 |
| JP | 6-283697 | A | | 10/1994 |
| JP | 2004-093791 | A | | 3/2004 |
| JP | 2004-093803 | A | | 3/2004 |
| WO | WO 2007030934 | A2 | * | 3/2007 |

OTHER PUBLICATIONS

Purdue University. "The Chemistry of the Halogens." (c) Apr. 14, 2009. Available from: < http://web.archive.org/web/20090414155348/http://chemed.chem.purdue.edu/genchem/topicreview/bp/ch10/group7.php >.*
Hanifi, D., et al. "Novel C3-symmetric n-type tris(aroyleneimidazole) and its analogs: synthesis, physical properties and self-assembly." Chem. Comm. (2011), vol. 47, pp. 3454-3456.*
PCT International Search Report for PCT/EP2012/060794 mailed Sep. 5, 2012 (3 pages).
Ameri et al., "Organic Tandem Solar Cells: A Review," Energy Environ. Sci., 2009, 2:347-363.
Babel et al., "High Electron Mobility in Ladder Polymer Field-Effect Transistors," J. Am. Chem. Soc., 2003, 125:13656-13657.
Erten et al., "Bilayer Heterojunction Solar Cell Based on Naphthalene Bis-Benzimidazle," Inorganica Chimica Acta, 2008, 361:595-600.
Feast et al., "Poly(4-vinyltriphenylamine): Synthesis and Application as a Hole Transport Layer in Light-Emitting Diodes," Polymer Bulletin, 1999, 42:167-174.
Herbst et al., "Industrial Organic Pigments, Production, Properties, Applications," Third Completely Revised Edition, Wiley-VCH, Weingheim, 1995, 473-487.
Hong et al., "Antenna Effects and Improved Efficiency in Multiple Heterojunction Photovoltaic Cells Based on Pentacene, Zinc Phthalocyanine, and C60," Journal of Applied Physics, 2009, 106:064511-1-064511-6.
Langhals et al., "Naphthalene Amidine Imide Dyes by Transamination of Naphthalene Bisimides," Chem. Eur. J., 2006, 12:2815-2824.
Liao et al., "Highly Efficient Inverted Polymer Solar Cell by Low Temperature Annealing of CS2CO3 Interlayer," Applied Physics Letters, 2008, 92:173303-1-173303-3.
Mizuguchi, "Crystal Structure and Electornic Characterization of trans- and cis-Perinone Pigments," J. Phys. Chem. B, 2004, 108:8926-8930.
Simon et al, "Optical Properties Engineering for Organic Solar Cells," Int. J. Materials and Product Technology, 34 (4):469-487, (c) 2009.
Tamuly et al., "Fluorescence Quencing and Enhancement by H-Bonding Interactions in Some Nitrogen Containing Fluorophores," Supramolecular Chemistry, 2006, 18(8):605-613.
Young et al., "Comparative PCET Study of a Donor—Acceptor Pair Linked by Ionized and Nonionized Asymmetric Hydrogen-Bonded Interfaces," J. Am. Chem. Soc., 2009, 131:7678-7684.

* cited by examiner

Primary Examiner — Andrew D Kosar
Assistant Examiner — John S Kenyon
(74) Attorney, Agent, or Firm — Sutherland Asbill & Brennan LLP (57) ABSTRACT

The present invention relates to new naphthalene carbodiimide (NTCDI) derivatives, and organic electronic device using the same and especially to an organic solar cell. The new NTCDI derivatives are used as acceptor, electron transport material, and doped electron transport materials.

9 Claims, 1 Drawing Sheet

COMPOUND FOR ORGANIC ELECTRONIC DEVICE

TECHNICAL FIELD

This invention is related to new compounds, organic electronic devices using the same and especially to organic photovoltaic (OPV) devices, also known as organic solar cells.

The solar light is one of the most attractive forms of renewable energy, because it is available in relatively large power density, and it is easily convertible into other forms of energy such as electrical, thermal, etc.

Organic solar cells are attracting considerable interest from research and industry; they offer a big promise for the efficient and large scale conversion of light into electricity. The production of organic solar cells is less material demanding than the production of inorganic crystalline solar cells. The production also consumes considerably less energy than the production of any other inorganic solar cell.

Efficiency of organic solar cells has been improving steadily. In 2008 a certified power conversion efficiency value of 5% was reached, and in 2010 the psychological barrier of 8% was broken, aligning the efficiency of the organic solar cells to typical values of amorphous Si devices.

BACKGROUND ART

OPV devices have the most different devices architectures. Typically they comprise at least one organic semiconducting layer between two electrodes. That organic layer can be a blend of a donor and an acceptor such as P3HT (poly3-hexyl-tiophene) and PCBM (phenyl Cn Butyric Acid Methyl Ester). Such simple device structures only achieve reasonably efficiencies if interfacial injection layers are used to facilitate charge carrier injection/extraction (Liao et al., Appl. Phys. Lett., 2008. 92: p. 173303). Other organic solar cells have multi-layer structures, sometimes even hybrid polymer and small molecule structures. Also tandem or multi-unit stacks are known (Ameri et al., Energy & Env. Science, 2009. 2: p. 347). From those, the multi-layer devices can be easier optimized since different layers can comprise different materials which are suitable for different functions. Typical functional layers are transport layers, optically active layers, injection layers, etc.

Optically active materials are materials with a high absorption coefficient, for at least a certain wavelength range of the solar spectra, which materials convert absorbed photons into excitons which excitons contribute to the photocurrent. The optically active materials are typically used in a donor-acceptor heterojunction, where at least one of the donor or acceptor is the light absorbing material. The interface of the donor-acceptor heterojunction is responsible for separating the generated excitons into charge carriers. The heterojunction can be a bulk-heterojunction (a blend), or a flat (also called planar) heterojunction, additional layers can also be provided (Hong et al, J. Appl. Phys., 2009. 106: p. 064511).

The loss by recombination must be minimized for high efficiency OPV devices. Therefore, the materials in the heterojunction must have high charge carrier mobilities and high exciton diffusion lengths. The excitons have to be separated at the heterointerface and the charge carriers have to leave the optically active region before any recombination takes place. For those reasons, only few organic materials are suitable to be used in the heterojunction. For instance, currently, there are no known materials which can compete with the fullerenes and their derivatives (e.g. C60, C70, PCBM, and so on) as acceptor in OPV devices.

Transport materials are required to be transparent, at least in the wavelengths wherein the device is active, and have good semiconducting properties. Those semiconducting properties are intrinsic, such as energy levels or mobility, or extrinsic such as charge carrier density. The charge carrier density can be extrinsically influenced, for instance, by doping the material with an electrical dopant.

Although in steady development, the choice of materials for OPV is still very limited, especially for optically active materials and for electron transport materials. Some highly efficient device structures employ TiO as electron transport and optical spacer with the disadvantage of being difficult to deposit (Simon et al., Int. J. of Mat. & Prod. Tech., 2009. 34: p. 469). Other devices use Fullerene C60 as ETL which is not transparent enough for functioning as an optical spacer. Other materials such as NTCDA, although transparent and with good semiconducting properties, are not morphologically stable and crystallize even at room temperature.

The new materials can also be employed in OLEDs, and in OTFTs.

Almost no organic electron transport material is available with suitable semiconducting, chemical, and thermal properties.

TECHNICAL PROBLEM

It is the objective of the present invention to provide a new organic semiconductor material for use in organic electronic devices, preferably organic solar cells. The material is preferentially used in at least one of: an optically active layer and an electron transport layer, more preferentially at least in an electron transport layer.

SOLUTION OF THE PROBLEM

The object is achieved by compounds and organic electronic devices according to the independent claims 1 and 11. Preferred embodiments are disclosed in the sub-claims.

This object is especially achieved by an organic electronic device, especially an organic solar cell, comprising at least one compound according to the following formula (I):

Formula (I)

wherein
R1 is C5-20-aryl; C5-20-heteroaryl, C2-C20-alkyl, C2-C20-perfluoroalkyl;
each X is independently selected from C, N, O and S;
each R is independently selected from C5-20-aryl, C5-20-heteroaryl, $NO_2$, CN, H, F, $CF_3$, C2-C20-alkyl and C2-20-perfluoroalkyl;
m=0, 1, 2 or 3.

$C_5$-$C_{20}$-aryl is preferably selected from: phenyl, naphthyl, anthracyl, perfluorophenyl, fluorophenyl.

$C_5$-$C_{20}$-heteroaryl is preferably selected from pyridyl, thienyl, oxazolyl, imidazolyl, benzimidazolyl.

The term "aryl" means an aromatic group containing only carbon in the aromatic ring or rings. An aryl group may contain 1 to 3 separate, fused, or pendant rings and from 5 to 20 ring atoms, without heteroatoms as ring members. Examples of aryl groups include, but are not limited to, phenyl, naphthyl, including 1-naphthyl and 2-naphthyl, perfluorophenyl, fluorophenyl, and bi-phenyl.

ADVANTAGES OF THE COMPOUNDS

A compound according to formula (I) is preferentially used in an electron transport layer in a solar cell. The compound is the main component of the electron transport layer. Preferentially at least one electron transport layer comprising the compound according to formula (I) is doped with an electrical dopant.

In an alternative embodiment, or in addition, the compound according to formula (I) is used in an exciton blocking layer as its main component. The exciton blocking layer is preferentially also an electron transport layer. The layer has a low enough LUMO to transport electrons between the acceptor and the cathode, and at the same time, it has a high HOMO-LUMO gap to block the excitons confining them into the optically active region, which means that the HOMO-LUMO gap is larger than the HOMO-LUMO gap of any immediately (in contact) adjacent material from the optically active region. This layer is preferentially electrically undoped.

In another alternative embodiment, or in addition, the compound according to formula (I) is used as a main component of an exciton-and-hole-blocking-layer. In this embodiment, the exciton-and-hole-blocking-layer has a low enough HOMO to block holes from an adjacent layers (mainly from the donor molecule of the bulk-heterojunction), and at the same time, it has a high HOMO-LUMO gap to block the excitons out of its layer confining them into the optically active region, which means that the HOMO-LUMO gap is larger than the HOMO-LUMO gap of any immediately (in contact) adjacent material from the optically active region. This layer is preferentially electrically undoped.

In an alternative embodiment, or in addition, the compound according to formula (I) is an acceptor in a donor-acceptor heterojunction. In an aspect of this embodiment, the compound also harvest light which light is converted into charge and contributes to the photocurrent, preferentially, the contribution of the photocurrent at 0V is due to absorption of photons in the range of 350-800 nm, more preferably in the range of 350-500 nm. Preferentially the contribution is greater than 5%.

In an alternative embodiment, or in addition to the use as an acceptor, the compound according to formula (I) is used as main component of an exciton-blocking and electron-transporting layer. In this embodiment, the exciton-blocking-and-electron-transporting-layer has low enough LUMO to accept the electron from a donor molecule in an adjacent layer, and at the same time, it has a high HOMO-LUMO gap to block the excitons out of its layer confining them into the optically active region, which means that the HOMO-LUMO gap is larger than the HOMO-LUMO gap of any immediately (in contact) adjacent material from the optically active region. This layer is preferentially electrically undoped.

The compound according to formula (I) is preferentially used as main component of a layer in combination with an adjacent layer, wherein the modulus(absolute value) of the difference of the LUMO of the layer and the adjacent layer is smaller 0.4 eV, more preferentially smaller than 0.2 eV (0.2 eV is about the width of the density of states of one material).

Preferentially the adjacent layer comprises as its main component a fullerene chosen from $C_{58}$, $C_{60}$, $C_{70}$, or a soluble derivative of it (e.g. $PC_{60}BM$).

In another aspect of the invention, an organic solar cell comprises a compound according to the Formula (I), in a layer adjacent to the donor-acceptor heterojunction, in an undoped form. In addition, the organic solar cell comprises an additional doped layer comprising a compound according to the Formula (I) between the layer adjacent to the donor-acceptor heterojunction and the cathode.

In another aspect of the invention, the solar cell is a polymer solar cell, comprising at least one semiconducting polymer in the at least one donor-acceptor heterojunction and comprising the compound according to formula (I) in at least one electron transport layer. Preferentially at least one electron transport layer is n-doped.

In a preferred aspect of the invention, the organic solar cell comprises a pi, ni, or pin structure, comprising a first p, i, or n layer each. Here, p denotes a p-doped hole transport layer, n denotes a n-doped electron transport layer, and i is an intrinsic photoactive layer. The transport layers have a greater HOMO-LUMO gap than the photoactive layer.

For all aspects of the invention, exemplary n-dopants which can be employed are: tetrathianaphthacene, [Ru(terpy) 2]⁰; rhodamine B; pyronin B chloride; acridine orange base; leuco crystal violet; 2,2'-diisopropyl-1,1',3,3'-tetramethyl-2, 2',3,3',4,4',5,5',6,6',7,7'-dodecahydro-1H,1'H-2,2-bibenzo [d]imidazole; 4,4',5,5'-tetracyclohexyl-1,1',2,2',3,3'-hexamethyl-2,2',3,3'-tetrahydro-1H,1'H-2,2'-bisimidazole; 2,2'-diisopropyl-4,4',5,5'-tetrakis(4-methoxyphenyl)-1,1',3,3'-tetramethyl-2,2',3,3'-tetrahydro-1H,1'H-2,2'-bisimidazole; 2-isopropyl-1,3-dimethyl-2,3,6,7-tetrahydro-1H-5,8-dioxa-1,3-diaza-cyclopenta[b]-naphthene; bis-[1,3-dimethyl-2-isopropyl-1,2-dihydro-benzimidazolyl-(2)]; tetrakis(1,3,4,6, 7,8-hexahydro-2H-pyrimido[1,2-a]pyrimidinato)ditungsten (II); 2,2'-diisopropyl-4,5-bis(2-methoxyphenyl)-4',5'-bis(4-methoxyphenyl)-1,1',3,3'-tetramethyl-2,2',3,3'-tetrahydro-1H,1'H-2,2'-bisimidazole; 2,2'-diisopropyl-4,5-bis(2-methoxyphenyl)-4',5'-bis(3-methoxyphenyl)-1,1',3,3'-tetramethyl-2,2',3,3'-tetrahydro-1H,1'H-2,2'-bisimidazole (see for example, patent publications US 2005/0040390, US 2009/0212280, and US 2007/0252140).

Devices

Figure 1:
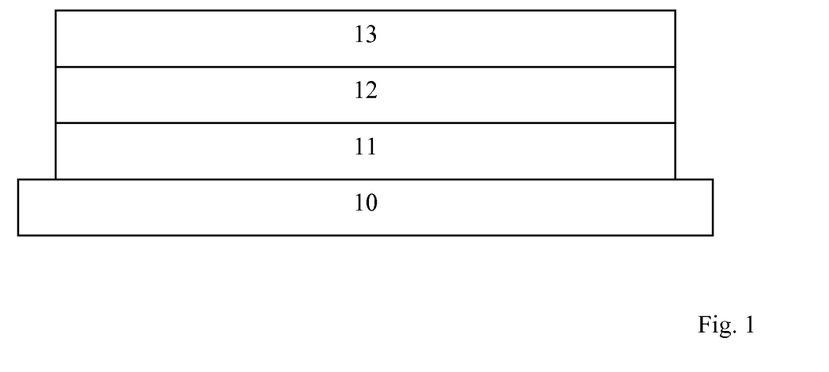
FIG. 1 is a simple diagram representing the stack of layers which forms a solar cell.

According to FIG. 1, an organic solar cell comprises at least a substrate (10), an anode (11), at least one organic optically active layer (12), and a cathode (13). The stack of layers can also be inverted, wherein layer (11) would be the cathode, and layer (12) would be the anode. Normally the layers do not overlap 100% so that extensions of the layers used for the electrodes are used for electrical connections, but other configurations are possible.

In one embodiment, the substrate (10) is a transparent substrate, such as a glass, or polymeric plate or web; the anode (11) is a transparent conducting oxide, such as ITO, FTO, AlZO; and the cathode (13) comprises aluminum or an aluminum alloy. In one embodiment the at least one organic optically active layer (12) comprises a blend of a thiophene containing polymer and a compound according to formula (I). Alternatively the at least one organic optically active layer (12) comprises a blend of a donor polymer, preferentially a thiophene containing polymer, and an acceptor, preferentially a fullerene or a soluble fullerene derivative; in this embodiment a layer containing the compound according to Formula (I) is formed between the at least one organic optically active layer (12) and the cathode (13). Optionally the layer structure is inverted. The transparent conducting oxide can be replaced by another transparent conducting material, for example a thin metal layer, carbon nanotubes, conducting polymer, or metal nanowires.

In one embodiment the anode (11) is not transparent and mainly comprises Aluminum or an Aluminum alloy. The substrate (10) is not necessarily transparent. The cathode (13) comprises a transparent conducting oxide layer or a thin (thickness<30 nm) transparent metal layer.

Still in connection to FIG. 1, in another embodiment, the substrate (10), the anode (11), and the cathode (13) are transparent. In this embodiment, the overall device is semi-transparent, because it does not have 100% absorption of the incident light for any wavelength in the visible range of wavelengths.

Note that multiple stacked devices (e.g. tandem devices) are also provided in this invention. In such devices at least one additional organic optically active layer is formed between the at least one organic optically active layer (12) and the cathode (13). Additional organic or inorganic layers may be used to provide a suitable electronic connection and optical optimization of the layer position. Preferentially, at lest parts of these functions are provide by layers comprising a compound according to the formula (I).

Still in connection to FIG. 1, surface treatment of the electrodes, buffer layers, and/or injection layers can be used to provide efficient charge carrier injection/extraction. Examples of surface treatments are acid, or plasma treatment of the electrode's surface. Example of injection layers are thin inorganic insulating layers (e.g. LiF) and thin electrical dopant layers.

Figure 2:
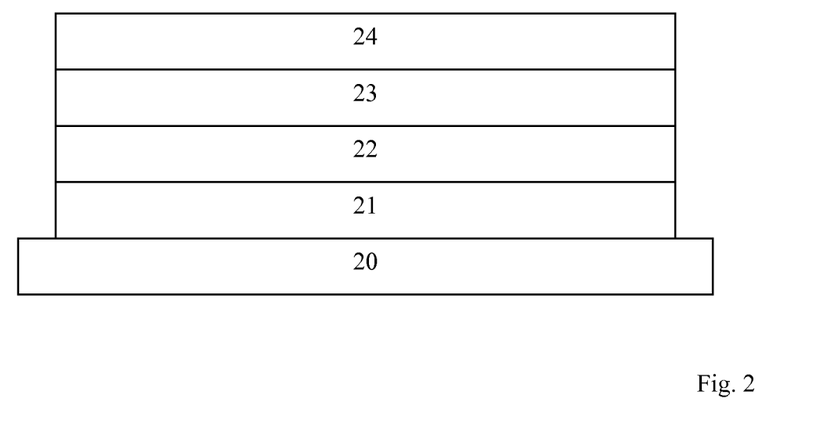
FIG. 2 is a simple diagram representing the layers of a solar cell comprising an ETL.

FIG. 2 shows a stack of layers representing an organic solar cell comprising at least: a substrate (20), an anode (21), at least one optically active layer (22), an organic electron transport layer (ETL) (23), and a cathode (24). The stack of layers can also be inverted. The ETL is formed between cathode and optically active layer.

In one embodiment, the organic electron transport layer comprises as its main component a compound according to the Formula (I). Preferentially this compound according to the Formula (I) is doped with an electrical dopant. The ETL (23) can have any thickness, its thickness is preferably smaller than 40 nm in the case that there is no additional optically active layer between the at least one optically active layer (22) and the cathode (24).

All embodiments as described in connection to FIG. 1 can also be applied here, in connection to FIG. 2.

All figures are simple representations of the layered structure of a solar cell. Some device features are not shown such as electrical connections, encapsulation, optical structures which are external to the electrodes, etc. At least one of the electrodes (anode and cathode) is transparent in the wavelength range in which the device is active.

In another embodiment the at least one optically active layer (22) is a donor-acceptor bulk heterojunction (blend of donor-acceptor). The donor is preferentially formed by a strong absorbing compound comprising a pyrrole or a thiophene group. The acceptor is preferentially a $C_{58}$, $C_{60}$, or $C_{70}$ fullerene or a soluble fullerene derivative. The ETL (23) comprises a compound according to the formula (I) as its main component. The ETL (23) is preferentially doped with an n-dopant. Or organic n-dopants are highly preferred due to their easier handling in production.

In another embodiment, the at least one optically active layer (22) is a donor-acceptor bulk heterojunction (blend of a donor with an acceptor). The donor is preferentially formed by a strong absorbing compound comprising a pyrrole or a thiophene group. The acceptor is a compound according to Formula (I).

In one aspect of the invention, all organic layers are constituted from small molecules. Preferentially, these small molecules can be deposited by VTE (Vacuum Thermal evaporation).

In another aspect of the invention, at least one organic semiconducting layer comprises a polymer and at least one additional semiconducting layer comprises a compound according to Formula (I).

Another aspect of the invention is a layer comprising a compound of Formula (I) and an n-dopant. The invented compounds have a special advantage of forming very stable n-doped layers with a relatively high conductivity.

The conductivity can be measured by the so-called 2-point or 4-point-method. Here, contacts of a conductive material, such as gold or indium-tin-oxide, are disposed on a substrate. Then, the thin film to be examined is applied onto the substrate, so that the contacts are covered by the thin film. After applying a voltage to the contacts the current is measured. From the geometry of the contacts and the thickness of the sample the resistance and therefore the conductivity of the thin film material can be determined. The four point or two point method give the same conductivity values for doped layers since the doped layers grant a good ohmic contact, otherwise the contact resistance has to be deducted from the 2-point method.

The temperature stability can also be measured with that method with the addition that the (undoped or doped) layer is heated stepwise, and after a waiting period the conductivity is measured. The maximum temperature, which can be applied to the layer without loosing the desired semiconducting properties, is then the temperature just before the conductivity breaks down. For example, a doped layer can be heated on the substrate with two electrodes, as disclosed above, in steps of 1° C., wherein after each step there is a waiting period of 10 seconds. Then the conductivity is measured. The conductivity changes with temperature and breaks down abruptly at a particular temperature. The temperature stability is therefore the temperature up to which the conductivity does not break down abruptly. The measurement is performed in vacuum or inert gas.

The properties of the many different used materials can be described by the position of their highest occupied molecular orbital energy level (HOMO, synonym of ionization potential), and the lowest unoccupied molecular orbital energy level (LUMO, synonym of electron affinity).

Preferred compounds and their synthesis will be described below.

Synthesis

General

The following schema describes the general synthesis for the compounds according to the invention.

Further information on syntheses can be found in the following literature:

W. Herbst, K. Hunger: *Industrial Organic Pigments, Production, Properties, Applications, Third*, completely revised edition. p. 473-487, Wiley-VCH, Weinheim 1995.

Babel et al. (2003). "*High Electron Mobility in Ladder Polymer Field-Effect Transistors.*" *Journal of the American Chemical Society* 125(45), p. 13656-13657.

Erten and Icli (2008). "*Bilayer heterojunction solar cell based on naphthalene bis-benzimidazole.*" *Inorganics Chimica Acta* 361(3), p. 595-600.

Feast et al. (1999). "*Poly(4-vinyltriphenylamine). Synthesis and application as a hole transport layer in light-emitting diodes.*" *Polymer Bulletin (Berlin)* 42(2), p. 167-174.

Langhals and Jaschke (2006). "*Naphthalene amidine imide dyes by transamination of naphthalene bisimides.*" *Chemistry—A European Journal* 12(10), p. 2815-2824.

Mizuguchi, J. (2004). "*Crystal Structure and Electronic Characterization of trans- and cis-Perinone Pigments.*" *Journal of Physical Chemistry B* 108(26), p. 8926-8930.

Tamuly et al. (2006). "*Fluorescence quenching and enhancement by H-bonding interactions in some nitrogen containing fluorophores.*" *Supramolecular Chemistry* 18(8), p. 605-613.

Young et al. (2009). "*Comparative PCET Study of a Donor-Acceptor Pair Linked—by Ionized and Nonionized Asymmetric Hydrogen-Bonded Interfaces*" *J. Am. Chem. Soc.* 131, p. 7678-7684.

Compounds with m=0

Modifying the general synthesis to the form below enables the synthesis of the compounds with m=0:

R1-NH2 can be, for example: Aniline, 2-aminopyridine, 2-aminothiophene, 1,1,2,2,3,3,3-heptafluoropropan-1-amine, propan-1-amine

The structure can be, for example: 2,3-diaminobut-2-enedinitrile, 1,2-ethenediamine, (Z)-1,2-difluoroethene-1,2-diamine, (Z)-1,2-diphenylethene-1,2-diamine, (Z)-1,2-di(pyridin-2-yl)ethene-1,2-diamine, (Z)-1,2-di(thiophen-2-yl)ethene-1,2-diamine.

For m=0, it is preferably that R is different than NO2.

(1)

(2)

(3)

(4)

(22)

(23)

(24)

(25)

(26)

(27)

(28)

(29)

(30)

(31)

(32)

Compounds with m=1

Modifying the general synthesis to the form below enables the synthesis of the compounds with m=1:

The compounds R1-NH2 can be selected from those already disclosed above.

The structure can be, for example: 4,5-diaminophthalonitrile, 5,6-diaminopyrazine-2,3-dicarbonitrile, benzene-1,2-diamine, 5,6-dinitropyrazine-2,3-diamine, 5,6-difluoropyrazine-2,3-diamine, 4,5-difluorobenzene-1,2-diamine, 4,5-bis(trifluoromethyl)benzene-1,2-diamine, 5,6-bis(trifluoromethyl)pyrazine-2,3-diamine, 5,6-diphenylpyrazine-2,3-diamine, [1,1':2',1''-terphenyl]-4',5'-diamine, 4,5-bis(1-phenyl-1H-benzo[d]imidazol-2-yl)benzene-1,2-diamine, 5,6-bis(1-phenyl-1H-benzo[d]imidazol-2-yl)pyrazine-2,3-diamine, Preferred compounds are:

(33)

(34)

(35)

(36)

(37)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

-continued

(75)

(76)

(77)

(78)

(79)

(80)

(81)

-continued (82)

(83)

(84)

(85)

(86)

(87)

-continued

(88)

(89)

Compounds with m=2 or m=3

Modifying the general synthesis to the form below enables the synthesis of the compounds with m=2:

The compounds R1-NH2 can be selected from those already disclosed above.

The structure can be, for example: 6,7-diaminoquinoxaline, 2,3-phenazinediamine, 2,3-diamino-7-chlorophenazine, 6,7-Dimethyl-2,3-Quinoxalinediamine, 2,3-Quinoxalinediamine,

(90)

(91)

(92)

(93)

(94)

(95)

(96)

(97)

-continued

(98)

(99)

(100)

(101)

(102)

(103)

(104)

(105)

-continued (106)

(107)

(108)

(109)

(110)

(111)

(112)

-continued (113)

Synthesis of Compound (55)

First step: Synthesis of 7-phenyl-1H-isochromeno[6,5,4-def]isoquino line-1,3,6,8(7H)-tetraone(1). All manipulations were carried out in air, without any further purification of commercial solvents/chemicals.

Chemical Formula: $C_{14}H_4O_6$
Molecular Weight: 268, 178

Chemical Formula: $C_6H_7N$
Molecular Weight: 93, 126

Chemical Formula: $C_{20}H_9NO_5$
Molecular Weight: 343, 29

NTCDA (12 g, 44.7 mmol) was heated at 150° C., under stirring, in 315 mL dry DMF. Aniline (700 mg, 7.54 mmol) in solution in DMF (135 mL) is then added within 20 min. The mixture is stirred at 150° C. for an additional 6.5 hours before let cooled down overnight. The obtained precipitate (NTCDA) is then filtered to remove the excess NTCDA. The filtrate is reduced to a ⅓$^{rd}$, cooled down (fridge, 30 min), so that another fraction of NTCDA precipitates. The mixture is then filtered to separate the remaining NTCDA from the product. The filtrate is concentrated until almost dry and stirred 3 times with 200 mL Water in an ultrasonic bath. The product is finally filtered and washed with 50 mL water and dried in a vacuum oven overnight.

The obtained product is then dissolved in chloroform and filtered over celite. The solvents were evaporated and the material was used as such into the second step.

Yield: 2.9 g, GCMS purity: 92%

Second step: Synthesis of 9,10-difluoro-2-phenylbenzo[lmn]benzo[4,5]imidazo[2,1-b][3,8]phenanthroline-1,3,6(2H)-trione (2). All manipulations were carried out in air, without any further purification of commercial solvents/chemicals.

Scheme 2: Synthetic pathway step 2

Chemical Formula: $C_{20}H_9NO_5$
Molecular Weight: 343, 289

Chemical Formula: $C_6H_6F_2N_2$
Molecular Weight: 144, 122

135° C.
Eisessig (2)

Chemical Formula: $C_{26}H_{11}F_2N_3O_3$
Molecular Weight: 451, 38

In a 500 mL flask were added (1) (5.18 g, 15 mmol), 4,5-difluorobenzene-1,2-diamine (2.71 g, 18.8 mmol) and 300 mL acetic acid. The mixture is stirred 22 hours at 135° C., during which time a precipitate appears. The reaction medium is cooled down to room temperature and filtered using a Glass fritt (por 4). The precipitate is washed 6 times with 50 mL water and twice with 15 mL ethanol. The obtained red material is stirred in 50 mL chloroform for one hour before being filtered and washed twice with 20 mL chloroform. The obtained powder is dried overnight in a vacuum oven (40° C.) and dried over an oil pump for 6 hours at room temperature.

Yield: red powder, 6.6 g (97.5%).

HPLC purity after sublimation: 97%

Conductivity Tests

Compound (55) has a very high conductivity in a doped form, if compared to other organic ETMs. The conductivity at room temperature is $1.06 \cdot 10^{-3}$ S/cm and the stability temperature is 153° C. for a layer doped with Tetrakis(1,3,4,6,7,8-Hexahydro-2H-pyrimido[1,2-a]pyrimidinato)ditungsten (II). The conductivity at room temperature is $1.2 \cdot 10^{-2}$ S/cm and the stability temperature is 141° C. for a layer doped with 4,4',5,5'-tetracyclohexyl-1,1',2,2',3,3'-hexamethyl-2,2',3,3'-tetrahydro-1H,1'H-2,2'-biimidazole.

Nomenclature

Inverted—The term inverted solar cell, or inverted structure, refers to a device with a layer structure in which the cathode is closer to the substrate than the anode. In the method of production of an inverted device, the cathode is formed on the substrate, following the deposition of the organic and other layers, which are followed by the deposition of the cathode.

ETL—electron transport layer, is a layer which is used in a device stack in such a way that the main charge carriers are electrons. Typically, this layer comprises an electron transport material (ETM). Hole blocking layers, exciton blocking layers between the cathode and its closest donor-acceptor heterojunction are also electron transport layers. Electron injection layers could also be electron transport layers, if they are semiconductors comprising an ETM.

ETM—electron transport material is a semiconducting material which is stable towards reduction and has a high mobility for electrons. In an ETM, the electron mobility is typically higher than the hole mobility.

HTL—hole transport layer, is a layer which is used in a device stack in such a way that the main charge carriers are electrons. Typically this layer comprises a hole transport material (HTM).

HTM—hole transport material is a semiconducting material which is stable towards oxidation and has a high mobility for holes. In a HTM, the hole mobility is typically higher than the electron mobility.

FHJ—Flat heterojunction, is a donor-acceptor heterojunction in which the donor and acceptor materials are in separate layers. Preferentially the donor and acceptor materials are in adjacent layers providing a hetero-interface. Alternatively, other layers can be placed in between, to assist the light absorption and/or charge carrier separation.

BHJ—Bulk heterojunction, is a mixed layer comprising a donor, an acceptor, and an absorbing material. Typically at least one of the donor and acceptor materials are also the absorbing material. The donor-acceptor heterointerface is necessary for the separation of the excitons formed by photoabsorbtion into charge carriers. A bulk heterojunction can be graded, or also comprise additional layers. A bulk donor-acceptor heterojunction can also be a hybrid junction, comprising a mixed layer and at least one layer comprising: the acceptor but no donor material, or the donor but no acceptor material. Such a heterojunction can also be a graded bulk heterojunction.

Acceptor—Acceptor, in this invention, is a compound used in an optically active layer of a solar cell to assist the excitonic separation into charge carriers, accepting the electron. The term acceptor must not be confused with an electrical p-dopant which is a very strong acceptor capable of doping a hole transport layer.

Donor—Donor, in this invention, is a compound used in an optically active layer of a solar cell to assist the excitonic separation into charge carriers, donating an electron (accepting a hole). The term donor must not be confused with an electrical n-dopant which is a very strong donor capable of doping an electron transport layer.

Electrical dopant—Electrical dopant is a dopant which is capable to, when added to a semiconductor, increase its charge carrier density, consequently increasing its conductivity. The increase in charge carrier density is due to a charge transfer between the LUMO and HOMO of the at least two components of the dopant-semiconductor system. The term electrically doped refers to a layer or material which is doped by an electrical dopant, as defined above.

n-dopant—electrical dopant capable of increasing the density of negative charge carriers in an electron transport material or electron transport layer. The negative charge carriers are provided on the effective conduction band of the electron transport layer (typically the LUMO of the electron transport material).

p-dopant—electrical dopant capable of increasing the density of positive charge carriers in a hole transport material or hole transport layer. The positive charge carriers are provided on the effective valence band of the hole transport layer (typically the HOMO of the hole transport material).

Transparency—those transport layers, which do not contribute to the photocurrent generation, are required to be transparent to avoid any efficiency loss due to undesired absorption. A high transparency is required in the range of wavelengths in which the solar cell is active. A high transparency preferentially means an extinction coefficient (k) smaller than 1, more preferably smaller than 0.1.

LUMO—Lowest unoccupied molecular orbital.

HOMO—Highest occupied molecular orbital.

Intrinsic layer—a layer which is not doped with dopants which increases the charge carrier density in the layer. Here it is considered that the layer in the dark, and no temperature gradient, or electrical field is applied to it.

The features disclosed in the foregoing description, in the claims and in the accompanying drawings may both separately and in any combination be material for realizing the invention in diverse forms thereof.

The invention claimed is:
1. An organic electronic device, comprising at least one first electron transport layer, wherein the at least one first electron transport layer is n-doped and comprises at least one compound according to the following formula (I):

Formula (I)

wherein
R$_1$ is selected from C5-20-aryl, C5-20-heteroaryl, C2-C20-alkyl, or C2-C20-perfluoroalkyl;
each X is independently selected from C, N, O, or S;
each R is independently selected from C5-20-aryl, C5-20-heteroaryl, NO$_2$, CN, H, F, CF3, C2-C20-alkyl, or C2-20-perfluoroalkyl; and
m is 0, 1, 2 or 3.

2. The organic electronic device according to claim 1 further comprising a second electron transport layer wherein the second electron transport layer is undoped, and wherein the second electron transport layer is adjacent to a donor-acceptor heterojunction and the first electron transport layer is arranged between the second electron transport layer and a cathode.

3. The organic electronic device according to claim 2, wherein the second electron transport layer is a hole blocking and/or exciton blocking layer.

4. The organic electronic device according to claim 1, further comprising a donor-acceptor heterojunction, wherein the donor-acceptor heterojunction comprises the material according to formula (I).

5. The organic electronic device according to claim 4, wherein at least 5% of the photocurrent at 0V is due to absorption of photons in the range of 300-500 nm.

6. The organic electronic device according to claim 4, wherein the donor-acceptor heterojunction is a bulk-heterojunction.

7. The organic electronic device according to claim 1, further comprising at least one semiconductor polymer layer.

8. The organic electronic device according to claim 1, wherein the organic electronic device is a solar cell.

9. The organic electronic device according to claim 4, wherein the material according to formula (I) is an acceptor.

* * * * *